United States Patent
Kim et al.

(10) Patent No.: US 9,528,949 B2
(45) Date of Patent: Dec. 27, 2016

(54) METHODS OF DETECTING INHOMOGENEITY OF A LAYER AND APPARATUS FOR PERFORMING THE SAME

(71) Applicant: Samsung Electronics Co., Ltd., Suwon-Si (KR)

(72) Inventors: Jung-Hoon Kim, Hwaseong-si (KR); Jin-A Ryu, Hwaseong-si (KR); Chang-Ho Lee, Suwon-si (KR); Dong-Won Kim, Hwaseong-si (KR); Jae-Ho Kim, Hwaseong-si (KR); Jung-Dae Park, Ansan-si (KR); Nae-Ry Yu, Suwon-si (KR); Pil-Kwon Jun, Seoul (KR)

(73) Assignee: Samsung Electronics Co., Ltd. (KR)

( * ) Notice: Subject to any disclaimer, the term of this patent is extended or adjusted under 35 U.S.C. 154(b) by 276 days.

(21) Appl. No.: 14/197,737

(22) Filed: Mar. 5, 2014

(65) Prior Publication Data

US 2014/0270078 A1  Sep. 18, 2014

(30) Foreign Application Priority Data

Mar. 13, 2013 (KR) ........................ 10-2013-0026683

(51) Int. Cl.
*G01N 23/20* (2006.01)

(52) U.S. Cl.
CPC ... *G01N 23/20025* (2013.01); *G01N 2223/611* (2013.01)

(58) Field of Classification Search
CPC ................. G01N 23/20025; G01N 2223/611
See application file for complete search history.

(56) References Cited

U.S. PATENT DOCUMENTS

| | | | | |
|---|---|---|---|---|
| 4,999,014 | A * | 3/1991 | Gold | G01N 21/211 356/369 |
| 5,003,569 | A * | 3/1991 | Okada | G01B 15/02 378/54 |
| 5,671,044 | A | 9/1997 | Shimada et al. | |
| 5,771,061 | A * | 6/1998 | Komurasaki | B41J 2/473 347/242 |
| 7,072,442 | B1 * | 7/2006 | Janik | G21K 1/06 378/145 |
| 7,187,444 | B2 | 3/2007 | Naya et al. | |
| 7,664,608 | B2 | 2/2010 | Urano et al. | |
| 7,746,461 | B2 | 6/2010 | Aizawa et al. | |

(Continued)

FOREIGN PATENT DOCUMENTS

| | | |
|---|---|---|
| JP | 2007-057521 | 3/2007 |
| JP | 2008-014696 | 1/2008 |

(Continued)

*Primary Examiner* — Brooke Purinton
(74) *Attorney, Agent, or Firm* — Myers Bigel, P.A.

(57) ABSTRACT

In a method of detecting inhomogeneity of a layer, an incident light may be irradiated to at least two regions of the layer at a first incident angle position. First reflected lights reflected from the two regions of the layer may be sensed. The incident light may be irradiated to the at least two regions of the layer at a second incident angle position. Second reflected lights reflected from the two regions of the layer may be sensed. The first reflected lights and the second reflected lights may be compared with each other to obtain the inhomogeneity of the layer. Thus, the layer having a spot may be found.

17 Claims, 8 Drawing Sheets

(56) References Cited

U.S. PATENT DOCUMENTS

| | | | |
|---|---|---|---|
| 2005/0018183 A1* | 1/2005 | Shortt | G01B 11/0633 356/239.1 |
| 2006/0049349 A1* | 3/2006 | Shemesh | G01N 23/2252 250/310 |
| 2006/0063262 A1* | 3/2006 | Sopori | G01B 11/06 436/5 |
| 2007/0274447 A1* | 11/2007 | Mazor | G01N 23/201 378/70 |

FOREIGN PATENT DOCUMENTS

| | | |
|---|---|---|
| JP | 2008-292201 | 12/2008 |
| KR | 1020060057036 | 5/2006 |

\* cited by examiner

METHODS OF DETECTING INHOMOGENEITY OF A LAYER AND APPARATUS FOR PERFORMING THE SAME

CROSS-REFERENCE TO RELATED APPLICATIONS

This application claims priority under 35 USC §119 to Korean Patent Application No. 2013-26683, filed on Mar. 13, 2013 in the Korean Intellectual Property Office (KIPO), the contents of which are incorporated by reference in their entirety.

BACKGROUND

Generally, a pattern of a semiconductor device may be formed by coating a photoresist film on a layer, performing an exposing process on the photoresist film to form a photoresist pattern, and etching the layer using the photoresist pattern as an etch mask. Thus, in order to form the pattern having a desired shape, the photoresist pattern with a designed shape should be provided.

However, a spot may exist in the photoresist film. The spot may not be removed by the exposing process. The spot may cause inhomogeneity of the photoresist film. Therefore, the photoresist pattern may not have the desired shape due to a portion of the photoresist pattern where the spot may exist. As a result, in order to reduce the likelihood of an abnormal pattern being formed, it may be desirable to detect the inhomogeneity of the photoresist film.

SUMMARY

Example embodiments relate to methods of detecting inhomogeneity of a layer and apparatus for performing the same. More particularly, example embodiments relate to methods of detecting inhomogeneity of an organic layer caused by spots in the organic layer, and apparatus for performing the method.

Example embodiments provide methods of detecting inhomogeneity of a layer caused by a spot.

Example embodiments also provide apparatus for performing the above-mentioned methods.

According to example embodiments, there may be provided a method of detecting inhomogeneity of a layer. In the method of the inhomogeneity of the layer, an incident light may be irradiated to at least two regions of the layer at a first incident angle position. First reflected lights reflected from the two regions of the layer may be sensed. The incident light may be irradiated to the at least two regions of the layer at a second incident angle position. Second reflected lights reflected from the two regions of the layer may be sensed. The first reflected lights and the second reflected lights may be compared with each other to obtain the inhomogeneity of the layer.

In example embodiments, irradiating the incident light at the second incident angle may include moving a light source from the first incident angle position to the second incident angle position with the layer being fixed.

In example embodiments, irradiating the incident light at the second incident angle may include moving the layer from the first incident angle position to the second incident angle position with a light source being fixed.

In example embodiments, moving the layer from the first incident angle position to the second incident angle position may include rotating the layer with respect to an eccentric portion of the layer.

In example embodiments, comparing the first reflected lights and the second reflected lights with each other may include measuring total reflectivities of the first reflected lights and the second reflected lights, extracting reflectivities of no less than a total reflection angle from the total reflectivities, and comparing the reflectivities of no less than the total reflection angle with each other.

In example embodiments, the incident light may include a short-wavelength light. The short-wavelength light may include an X-ray.

In example embodiments, the layer may include an organic layer. The organic layer may include a photoresist film.

According to example embodiments, there may be provided an apparatus for detecting inhomogeneity of a layer. The apparatus may include an irradiating unit, a sensing unit, an incident angle-adjusting unit and a detecting unit. The irradiating unit may irradiate an incident light to at least two regions of the layer. The sensing unit may sense lights reflected from the layer. The incident angle-adjusting unit may provide the incident light with a first incident angle and a second incident angle. The detecting unit may compare the reflected lights to obtain the inhomogeneity of the layer.

In example embodiments, the incident angle-adjusting unit may include an adjusting shaft connected to irradiating unit, and an actuator for rotating the adjusting shaft.

In example embodiments, the incident angle-adjusting unit may include an adjusting shaft connected to an eccentric portion of the layer, and an actuator for rotating the adjusting shaft.

In example embodiments, the detecting unit may include a measuring member for measuring total reflectivities of the reflected lights, and a comparing member for extracting reflectivities of no less than a total reflection angle from the total reflectivities and for comparing the reflectivities of no less than the total reflection angle with each other.

According to example embodiments, the incident light having at least two incident angles may be irradiated to the at least two regions of the layer. The reflectivities totally reflected from a spot in the layer may be compared with each other to accurately detect the inhomogeneity of the layer. Thus, the layer having the spot may be previously found so that forming an abnormal pattern may be prevented.

According to example embodiments, a method of detecting inhomogeneity of a layer on a substrate includes: irradiating light from a light irradiating unit to a first region of the layer such that light is reflected from the first region of the layer; and irradiating light from the light irradiating unit to a second region of the layer such that light is reflected from the second region of the layer. The method includes, using a light sensing unit: sensing light reflected from the first region of the layer; and sensing light reflected from the second region of the layer. The method includes, using at least one controller: determining a reflectivity of the first region of the layer based on the sensed reflected light from the first region of the layer; determining a reflectivity of the second region of the layer based on the sensed reflected light from the second region of the layer; comparing the reflectivities of the first and second regions of the layer; and determining inhomogeneity of the layer based on the comparison of the reflectivities of the first and second regions of the layer.

BRIEF DESCRIPTION OF THE DRAWINGS

Example embodiments will be more clearly understood from the following detailed description taken in conjunction with the accompanying drawings.

FIG. 1 is a schematic illustration of an apparatus for detecting inhomogeneity of a layer in accordance with example embodiments;

FIG. 2 is a cross-sectional view illustrating paths of an incident light and a reflected light using the apparatus of FIG. 1;

FIG. 3 is a flow chart illustrating a method of detecting the inhomogeneity of the layer using the apparatus of FIG. 1;

FIG. 4 is a graph showing the inhomogeneity of the layer obtained using the method of FIG. 3;

FIG. 5 is a schematic illustration of an apparatus for detecting inhomogeneity of a layer in accordance with example embodiments;

FIG. 6 is a plan view illustrating an eccentric rotation of a stage in the apparatus of FIG. 5;

FIG. 7 is a flow chart illustrating a method of detecting the inhomogeneity of the layer using the apparatus of FIG. 5; and FIG. 8 is a graph showing the inhomogeneity of the layer obtained using the method of FIG. 7.

DETAILED DESCRIPTION OF THE EMBODIMENTS

Figure 1:
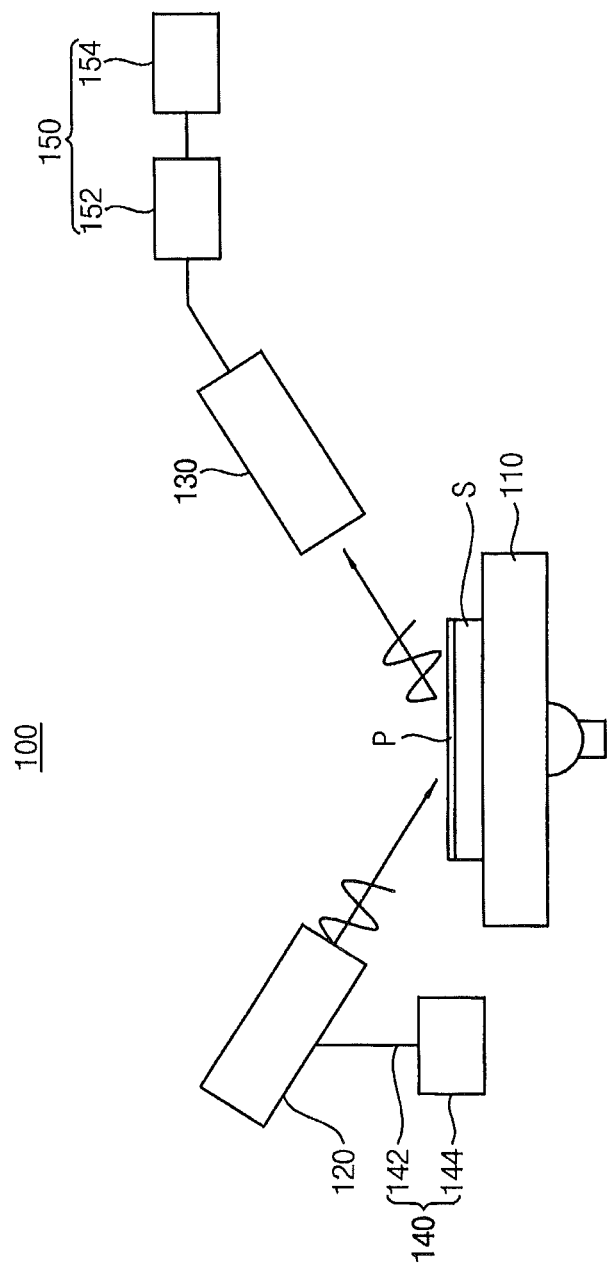
FIGS. 1 to 8 represent non-limiting, example embodiments as described herein.

Various example embodiments will be described more fully hereinafter with reference to the accompanying drawings, in which some example embodiments are shown. The present inventive concept may, however, be embodied in many different forms and should not be construed as limited to the example embodiments set forth herein. Rather, these example embodiments are provided so that this disclosure will be thorough and complete, and will fully convey the scope of the present inventive concept to those skilled in the art. In the drawings, the sizes and relative sizes of layers and regions may be exaggerated for clarity.

It will be understood that when an element or layer is referred to as being "on," "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. Like numerals refer to like elements throughout. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present inventive concept.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular example embodiments only and is not intended to be limiting of the present inventive concept. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to illustrations (e.g., cross-sectional illustrations) that are schematic illustrations of idealized example embodiments (and intermediate structures). As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of the present inventive concept.

Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, example embodiments will be explained in detail with reference to the accompanying drawings.

Figure 2:
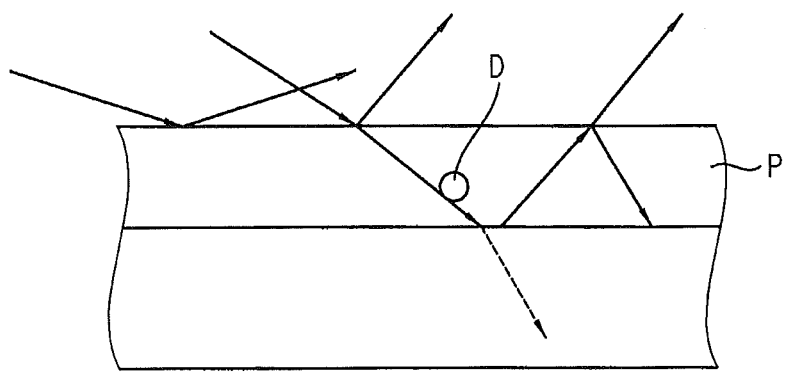

FIG. 1 is a schematic drawing illustrating an apparatus for detecting inhomogeneity of a layer in accordance with example embodiments, and FIG. 2 is a cross-sectional view illustrating paths of an incident light and a reflected light using the apparatus of FIG. 1.

Referring to FIG. 1, an apparatus or system 100 for detecting inhomogeneity of a layer in accordance with this example embodiment may include a stage 110, an irradiating unit or light source(s) 120, a sensing unit or sensor(s) 130, an incident angle-adjusting unit 140 and a detecting unit 150.

The stage 110 may be configured to support a semiconductor substrate S. In example embodiments, a layer P may be formed on the semiconductor substrate S. The layer P may include an organic layer such as a photoresist film. Alternatively, the layer P may include other layers in place of the organic layer.

The irradiating unit 120 may irradiate an incident light to the semiconductor substrate S. In example embodiments, the irradiating unit 120 may be positioned at one side of the stage 110 (e.g., at or above a left upper portion of the stage 110). Thus, the incident light irradiated from the irradiating unit 120 may be slantly irradiated to an upper surface of the semiconductor substrate S (e.g., irradiated at an angle relative to the upper surface of the substrate S). The irradiating unit 120 may irradiate the incident light to at least two regions of the photoresist film P. In example embodiments, the irradiating unit 120 may irradiate the incident light to a first region and a second region of the photoresist film P. The incident light may include a short-wavelength light. For example, the short-wavelength light may include an X-ray.

The sensing unit 130 may sense light reflected from the photoresist film P. In example embodiments, the sensing unit 130 may be positioned at an opposite side of the stage 110 from the irradiating unit 120 (e.g., at or above a right upper portion of the stage 110).

The incident angle-adjusting unit 140 may adjust incident angles of the incident light. Thus, the incident angle-adjusting unit 140 may adjust the irradiating unit 120 to provide the incident light with different incident angles. In example embodiments, the incident angle-adjusting unit 140 may provide the incident light with a first incident angle and a second incident angle. That is, the incident light may be irradiated to the photoresist film P from a first incident angle position and a second incident angle position (for example, the irradiating unit 120 may be moved or adjusted between the first and second incident angle positions). Therefore, the incident light may be irradiated to the first region of the photoresist film P at the first incident angle and the second incident angle. Further, the incident light may be irradiated to the second region of the photoresist film P at the first incident angle and the second incident angle.

In example embodiments, the incident angle-adjusting unit 140 may include an adjusting shaft 142 and an actuator 144. The adjusting shaft 142 may be connected to the irradiating unit 120. The actuator 144 may move (e.g., rotate or translate) the adjusting shaft 142 to move (e.g., rotate or tilt) the irradiating unit 120 from the first incident angle position to the second incident angle position. For example, the incident angle-adjusting unit 140 may be configured to tilt the irradiating unit 120 between the first and second incident angle positions.

The detecting unit 150 may compare the reflected lights sensed by the sensing unit 130 to detect the inhomogeneity of the photoresist film P. In example embodiments, the detecting unit 150 may include a measuring member or module 152 and a comparing member or module 154. The detecting unit 150 may include at least one controller configured to carry out the operations described below.

The measuring member 152 may measure total reflectivities of the reflected lights from the first region and the second region on the photoresist film P. The comparing member 154 may extract reflectivities of no less than a total reflection angle of the reflected lights from the first region and the second region on the photoresist film P from the total reflectivities. Further, the comparing unit 154 may compare the reflectivities of no less than the total reflection angle with each other to obtain the inhomogeneity of the photoresist film P.

Referring to FIG. 2, when a spot D having a relatively high density exists in the photoresist film P, a portion of the photoresist film P where the spot exists, for example the second region, may have a density higher than that of the first region of the photoresist film P. Thus, the reflectivities of the reflected lights totally reflected from the first region and the second region may be compared to each other to detect the spot in the first region of the photoresist film P. As a result, the inhomogeneity of the photoresist film P may be detected using the above-mentioned process.

Figure 3:
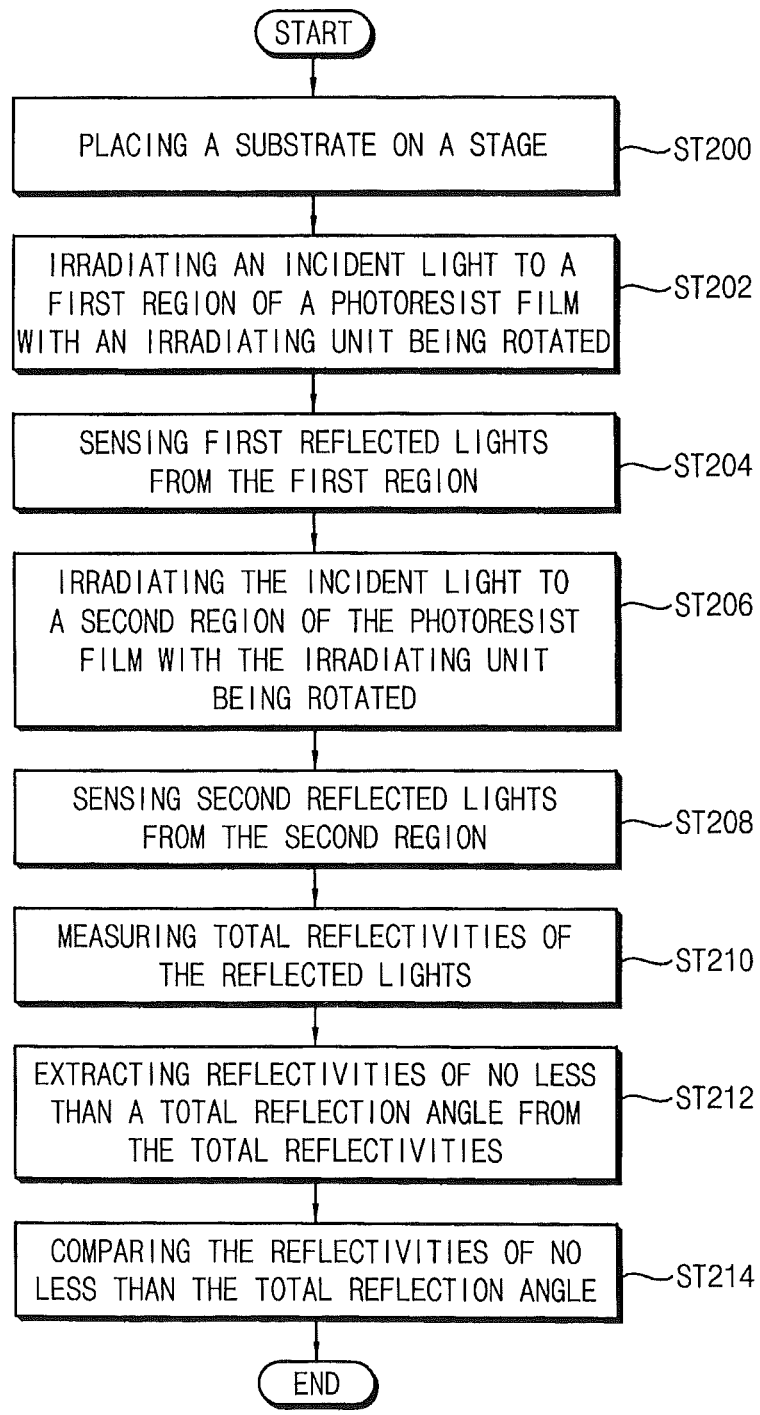

FIG. 3 is a flow chart illustrating a method of detecting the inhomogeneity of the layer using the apparatus in FIG. 1.

Referring to FIGS. 1 and 3, in step ST200, the semiconductor substrate S may be placed on the stage 110. The semiconductor substrate S may be aligned on the stage 110.

In step ST202, the irradiating unit 120 may irradiate the incident light to the first region of the photoresist film P. Simultaneously, the incident angle-adjusting unit 140 may rotate the irradiating unit 120. Therefore, the incident light irradiated to the first region of the photoresist film P may have the first incident angle and the second incident angle.

In step ST204, the sensing unit 130 may sense the first reflected lights from the first region of the photoresist film P.

In step ST206, the irradiating unit 120 may irradiate the incident light to the second region of the photoresist film P. Simultaneously, the incident angle-adjusting unit 140 may rotate the irradiating unit 120. Therefore, the incident light irradiated to the second region of the photoresist film P may have the first incident angle and the second incident angle.

In step ST208, the sensing unit 130 may sense the second reflected lights from the second region of the photoresist film P.

In step ST210, the measuring member 152 may measure the total reflectivities of the reflected lights sensed by the sensing unit 130. The measuring member 152 may measure the reflectivities using a following formula.

$$R = \frac{16\pi^2}{q^2} |F\{\rho(z)\}|^2$$

In the above formula, R may represent the reflectivity, q may indicate a scattering vector, $\rho(z)$ may represent a vertical electron density in the photoresist film and F may indicate a Fourier transform operator.

In step ST212, the comparing member 154 may extract reflectivities of reflected lights totally reflected from the photoresist film P among the total reflectivities.

In step ST214, the comparing member 154 may compare the reflectivities of no less than the total reflection angle with each other to detect the inhomogeneity of the photoresist film P.

Figure 4:
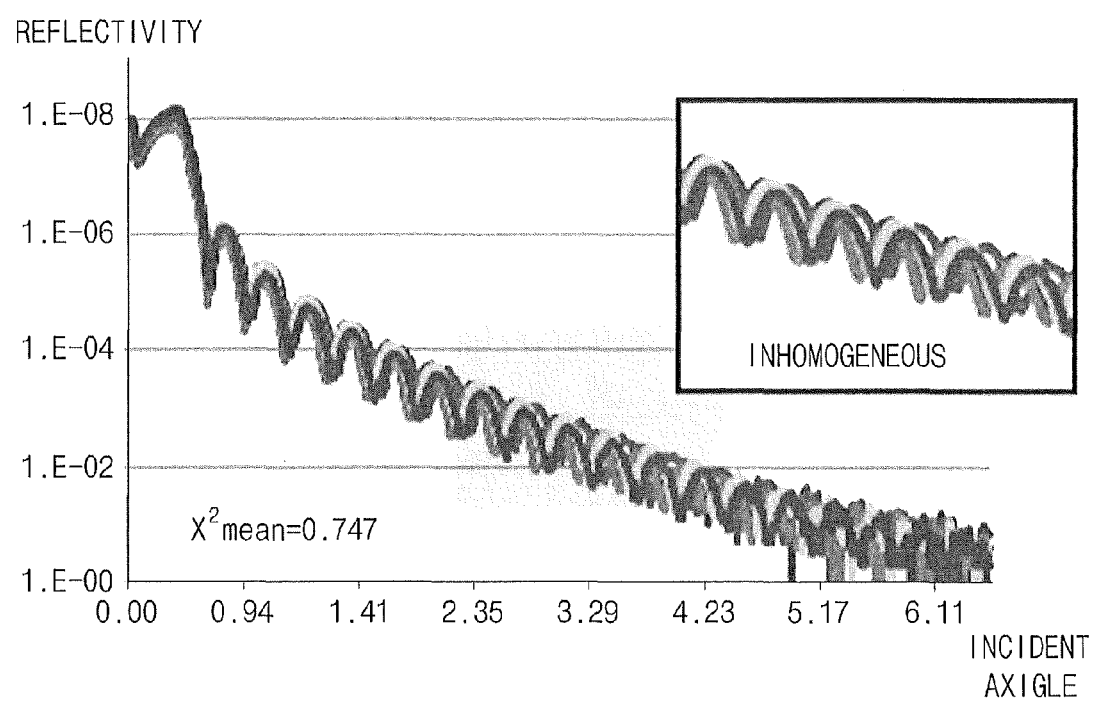

FIG. 4 is a graph showing the inhomogeneity of the layer obtained using the method in FIG. 3. In FIG. 4, a horizontal axis may represent the incident angle of the incident light, and the vertical axis may indicate the reflectivity of the reflected light.

The comparing member 154 may detect the inhomogeneity of the photoresist film P using a following formula.

$$\text{Inhomogeneity} = \left[\sum_{i=\theta_1}^{\theta_2} \left(\frac{R_i - R_{avg}}{R_i}\right)^2\right] / N$$

In the above formula, $R_i$ may represent the reflectivities by the incident angles, $R_{avg}$ may indicate an average reflectivity of the incident light at the same incident angle, and N may represent numbers of the incident angles.

Figure 5:
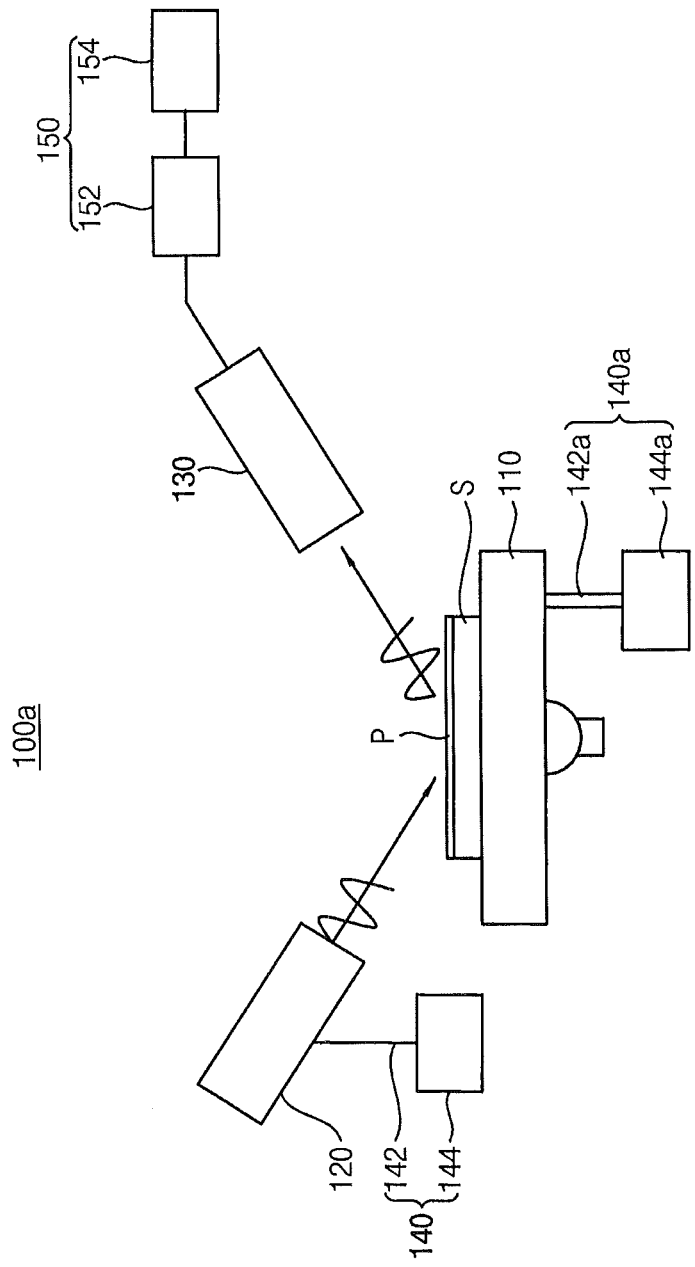
Figure 6:
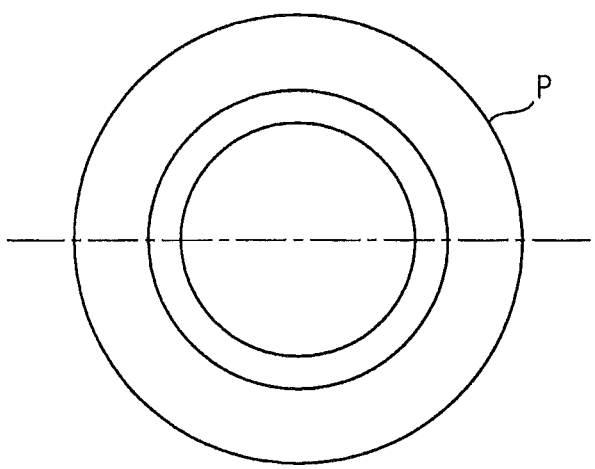

FIG. 5 is a schematic drawing illustrating an apparatus for detecting inhomogeneity of a layer in accordance with example embodiments, and FIG. 6 is a plan view illustrating an eccentric rotation of a stage in the apparatus of FIG. 5.

An apparatus 100a for detecting inhomogeneity of a layer in accordance with this example embodiment may include elements substantially the same as those of the apparatus 100 in FIG. 1 except for an incident angle-adjusting unit. Thus, the same reference numerals may refer to the same elements and any further discussion with respect to the same element may be omitted herein for brevity.

Referring to FIG. 5, an incident angle-adjusting unit 140a may include an adjusting shaft 142a and an actuator 144a. The adjusting shaft 142a may be connected to a lower surface of the stage 110. In example embodiments, the adjusting shaft 142a may be connected to an eccentric, off-center or outer portion of the stage 110, i.e., not a center point of the stage 110. Thus, when the actuator 144a rotates the adjusting shaft 142a, the stage 110 may be eccentrically rotated. Therefore, as shown in FIG. 6, the semiconductor substrate S on the stage 110 may also be eccentrically rotated. The angle-adjusting unit 140a or some other mechanism may also move or translate the stage 110 (and therefore the substrate S) and/or the irradiating unit 120 relative to one another (for example, move the stage 110 horizontally in the illustrated embodiment).

When the irradiating unit 120 irradiates the incident light to the semiconductor substrate S at the first incident angle position, the incident light may be concentrically irradiated to the photoresist film P. Thus, the incident light having the first incident angle may be incident to the first region and the second region of the photoresist film P.

When the stage 110 is horizontally moved, the irradiating unit 120 may irradiate the incident light to the photoresist film P at the second incident angle. Thus, the incident light having the second incident angle may be incident to the first region and the second region of the photoresist film P.

Figure 7:
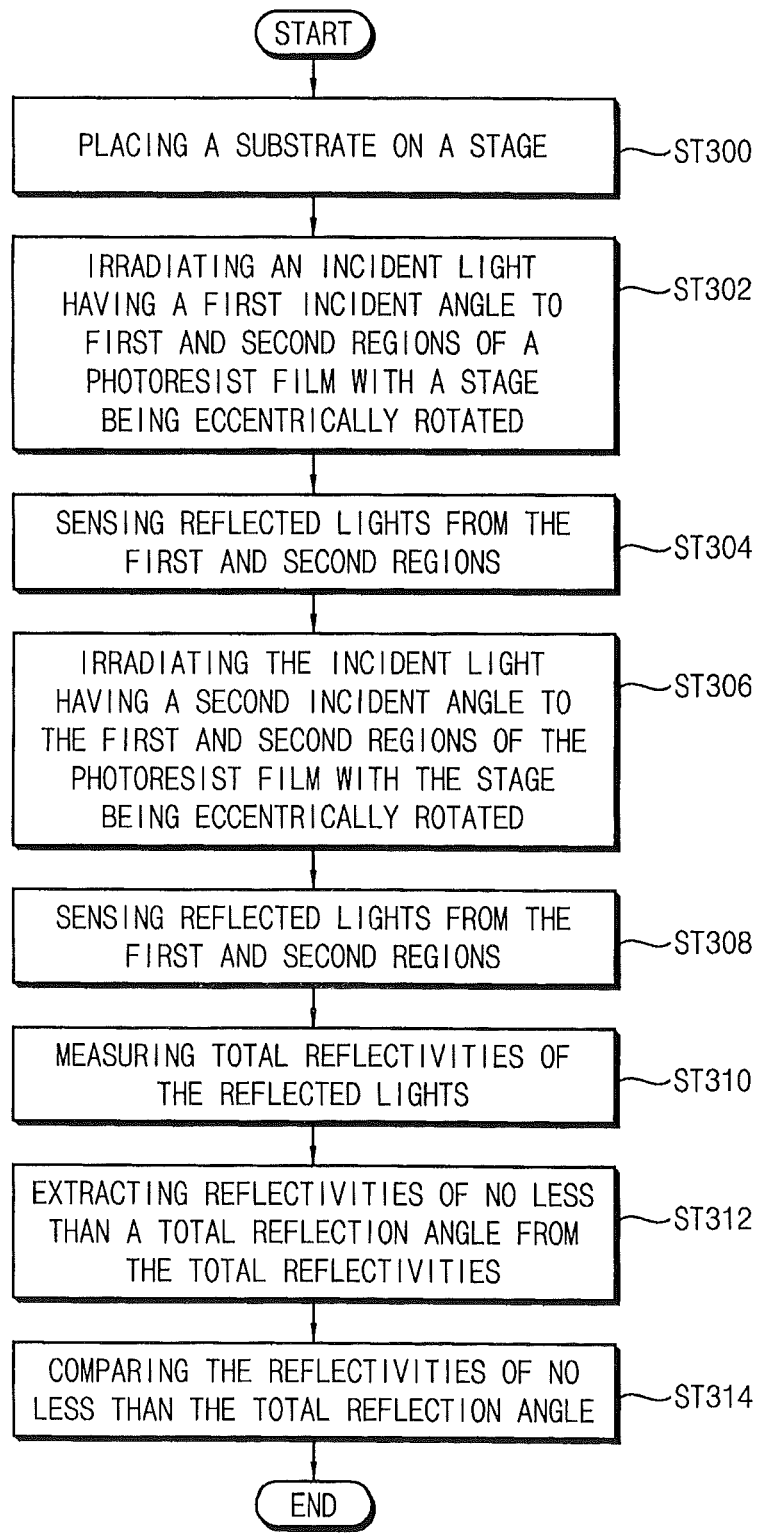

FIG. 7 is a flow chart illustrating a method of detecting the inhomogeneity of the layer using the apparatus in FIG. 5.

Referring to FIGS. 5 and 7, in step ST300, the semiconductor substrate S may be placed on the stage 110. The semiconductor substrate S may be aligned on the stage 110.

In step S302, the incident angle-adjusting unit 140a may eccentrically rotate the stage 110. The irradiating unit 120 may irradiate the incident light to the first region of the photoresist film P. Because the photoresist film P may be eccentrically rotated, the incident light having the first incident angle may be incident to the first region and the second region of the photoresist film P.

In step ST304, the sensing unit 130 may sense the first reflected lights from the first region of the photoresist film P.

In step ST306, when the stage 110 may be moved horizontally, the second incident angle may be provided between the irradiating unit 120 and the stage 110. The incident angle-adjusting unit 140a may eccentrically rotate the stage 110. The irradiating unit 120 may irradiate the incident light to the photoresist film P at the second incident angle. Because the photoresist film P may be eccentrically rotated, the incident light having the second incident angle may be incident to the first region and the second region of the photoresist film P.

In step ST308, the sensing unit 130 may sense the second reflected lights from the second region of the photoresist film P.

In step ST310, the measuring member 152 may measure the total reflectivities of the reflected lights sensed by the sensing unit 130. The measuring member 152 may measure the reflectivities using the formula described above in connection with step ST210.

In step ST312, the comparing member 154 may extract reflectivities of reflected lights totally reflected from the photoresist film P among the total reflectivities.

In step ST314, the comparing member 154 may compare the reflectivities of no less than the total reflection angle with each other to detect the inhomogeneity of the photoresist film P.

Figure 8:
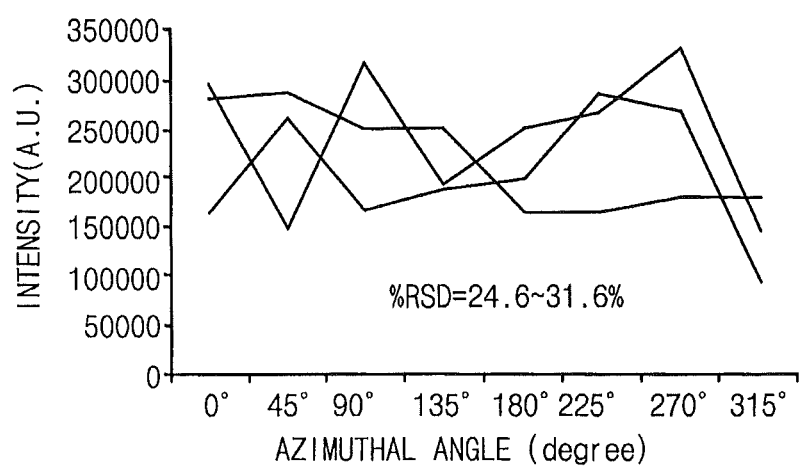

FIG. 8 is a graph showing the inhomogeneity of the layer obtained using the method in FIG. 3. In FIG. 8, a horizontal axis may represent an azimuthal angle (e.g., relative to the film P), and the vertical axis may indicate the reflectivity of the reflected light.

The comparing member 154 may detect the inhomogeneity of the photoresist film P using a following formula.

$$\% \, RSD = 100 \times \frac{\text{Standard deviation of } R_a}{\text{Average of } R_a}$$

In the above formula, % RSD may represent a relative standard deviation, and $R_a$ may indicate reflectivities by the azimuthal angle.

According to example embodiments, incident light having at least two incident angles may be irradiated to at least two regions of the layer. The reflectivities totally reflected from a spot in the layer may be compared with each other to detect the inhomogeneity of the layer with increased accuracy. Thus, the layer having the spot may be found in advance so that forming an abnormal pattern may be prevented.

The foregoing is illustrative of example embodiments and is not to be construed as limiting thereof. Although a few example embodiments have been described, those skilled in the art will readily appreciate that many modifications are possible in the example embodiments without materially departing from the novel teachings and advantages of the present inventive concept. Accordingly, all such modifications are intended to be included within the scope of the present inventive concepts defined in the claims.

What is claimed is:
1. A method of detecting inhomogeneity of a layer on a substrate, the method comprising:
   irradiating incident light to first and second regions of the layer at a first incident angle, wherein the incident light comprises an x-ray;
   sensing first reflected lights reflected from the first and second regions from the incident light irradiated at the first incident angle;
   irradiating incident light to the first and second regions of the layer at a second incident angle, wherein the incident light comprises an x-ray;
   sensing second reflected lights reflected from the first and second regions from the incident light irradiated at the second incident angle; and
   comparing the first reflected lights and the second reflected lights with each other to determine the inhomogeneity of the layer,
   wherein comparing the first reflected lights and the second reflected lights comprises:
      measuring total reflectivities of the first reflected lights and the second reflected lights;

extracting reflectivities of no less than a total reflection angle from the total reflectivities for each of the first and second reflected lights; and comparing the reflectivities of no less than the total reflection angle with each other.

2. The method of claim 1, further comprising moving a light source relative to the layer from a first incident angle position to a second incident angle position to irradiate the incident light at the second incident angle.

3. The method of claim 1, further comprising moving the layer from a first incident angle position to a second incident angle position relative to a light source to irradiate the incident light at the second incident angle.

4. The method of claim 3, wherein moving the layer from the first incident angle position to the second incident angle position comprises eccentrically rotating the layer.

5. The method of claim 1, wherein the layer comprises an organic layer.

6. The method of claim 5, wherein the organic layer comprises a photoresist film.

7. An apparatus for detecting inhomogeneity of a layer on a substrate, the apparatus comprising:
a stage for holding the substrate;
an irradiating unit configured to irradiate incident light to first and second regions of the layer, wherein the incident light comprises an x-ray;
an incident angle-adjusting unit configured to provide the incident light to the layer at a first incident angle and a second incident angle; and
a sensing unit configured to sense reflected lights from the layer including first reflected lights that are reflected from the irradiated light at the first region of the layer and second reflected lights that are reflected from the irradiated light at the second region of the layer;
a detecting unit configured to compare the first and second reflected lights with each other and to determine the inhomogeneity of the layer based on said comparison,
wherein the incident angle-adjusting unit comprises:
an adjusting shaft connected to an off-center portion of the stage; and
an actuator configured to rotate the adjusting shaft to eccentrically rotate the stage to move the layer between a first incident angle position wherein the incident light is provided at the first incident angle and a second incident angle position wherein the incident light is provided at the second incident angle.

8. The apparatus of claim 7, wherein the detecting unit is configured to:
measure total reflectivities of each of the first reflected lights and the second reflected lights;
extract reflectivities of no less than a total reflection angle from each of the total reflectivities; and
compare the reflectivities of no less than the total reflection angle with each other.

9. The apparatus of claim 7, wherein the layer comprises an organic layer.

10. A method of detecting inhomogeneity of a layer on a substrate, the method comprising:
placing the substrate on a stage;
with the layer in a first incident angle position, irradiating incident light from a light irradiating unit to first and second regions of the layer at a first incident angle, wherein the incident light comprises an x-ray;
using a light sensing unit, sensing first reflected lights from the first and second regions of the layer from the incident light irradiated at the first incident angle;
eccentrically rotating the stage to move the layer from the first incident angle position to a second incident angle position;
with the layer in the second incident angle position, irradiating incident light from the light irradiating unit to the first and second regions of the layer at a second incident angle, wherein the incident light comprises an x-ray;
using the light sensing unit, sensing second reflected lights from the first and second regions of the layer from the incident light irradiated at the second incident angle; and
using at least one controller, comparing the first reflected lights and the second reflected lights with each other to determine the inhomogeneity of the layer.

11. The apparatus of claim 9, wherein the organic layer comprises a photoresist film.

12. The method of claim 10, wherein comparing the first reflected lights and the second reflected lights comprises:
measuring total reflectivities of the first reflected lights and the second reflected lights;
extracting reflectivities of no less than a total reflection angle from the total reflectivities for each of the first and second reflected lights; and
comparing the reflectivities of no less than the total reflection angle with each other.

13. The method of claim 10, wherein the layer comprises an organic layer.

14. The method of claim 13, wherein the organic layer comprises a photoresist film.

15. The method of claim 4, wherein the irradiating incident light to the first and second regions of the layer at the first and second incident angles is carried out using an irradiating unit, and wherein the irradiating unit is fixed during the moving the layer from the first incident angle position to the second incident angle position.

16. The apparatus of claim 7, wherein the irradiating unit is fixed when the layer is moved between the first incident angle position and the second incident angle position.

17. The method of claim 10, wherein the light irradiating unit is fixed during the eccentrically rotating the stage to move the layer from the first incident angle position to the second incident angle position.

* * * * *